(12) United States Patent
Kim et al.

(10) Patent No.: US 12,177,327 B2
(45) Date of Patent: Dec. 24, 2024

(54) ENCRYPTION DEVICE AND OPERATION METHOD THEREOF

(71) Applicant: SAMSUNG ELECTRONICS CO., LTD., Suwon-si (KR)

(72) Inventors: Jae-hyeok Kim, Seoul (KR); Hong-mook Choi, Bucheon-si (KR); Ji-su Kang, Seoul (KR); Hyun-il Kim, Seongnam-si (KR); Jong-hoon Shin, Hwaseong-si (KR); Hye-soo Lee, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 342 days.

(21) Appl. No.: 17/245,309

(22) Filed: Apr. 30, 2021

(65) Prior Publication Data

US 2021/0284703 A1    Sep. 16, 2021

Related U.S. Application Data

(63) Continuation of application No. 16/157,242, filed on Oct. 11, 2018, now abandoned.

(30) Foreign Application Priority Data

Oct. 16, 2017    (KR) .................. 10-2017-0134252
Mar. 7, 2018    (KR) .................. 10-2018-0027082

(51) Int. Cl.
*H04L 9/00*    (2022.01)
*A61K 38/17*    (2006.01)
(Continued)

(52) U.S. Cl.
CPC .......... *H04L 9/002* (2013.01); *A61K 38/1793* (2013.01); *A61K 39/0011* (2013.01);
(Continued)

(58) Field of Classification Search
CPC ....................................................... H04L 9/002
See application file for complete search history.

(56) References Cited

U.S. PATENT DOCUMENTS 6,570,850 B1 *   5/2003   Gutierrez ............... H04L 47/16
                                                                370/231
7,848,515 B2    12/2010   Dupaquis et al.
(Continued)

FOREIGN PATENT DOCUMENTS

CN    101371480 A    2/2009
CN    105512055 A    4/2016
(Continued)

OTHER PUBLICATIONS

Communication dated Nov. 1, 2022 issued by the Korean Intellectual Office in Korean Patent Application No. 10-2018-0027082.
(Continued)

*Primary Examiner* — Simon P Kanaan
(74) *Attorney, Agent, or Firm* — Sughrue Mion, PLLC

(57) ABSTRACT

An encryption device for performing virtual and real operations and a method of operating the encryption device. The method includes performing a virtual operation; when a real operation request signal is received, determining whether the virtual operation being performed is completed; and in response to the virtual operation being completed, performing a real operation in response to the real operation request signal.

20 Claims, 12 Drawing Sheets

(51) Int. Cl.
*A61K 39/00* (2006.01)
*C07K 7/06* (2006.01)
*C07K 7/08* (2006.01)
*C07K 14/47* (2006.01)
*C07K 14/705* (2006.01)
*G01N 33/50* (2006.01)
*G01N 33/569* (2006.01)

(52) U.S. Cl.
CPC ............... *C07K 7/06* (2013.01); *C07K 7/08* (2013.01); *C07K 14/47* (2013.01); *C07K 14/4748* (2013.01); *C07K 14/705* (2013.01); *G01N 33/505* (2013.01); *G01N 33/5091* (2013.01); *G01N 33/56966* (2013.01); *G01N 33/56972* (2013.01); *A61K 2039/55566* (2013.01); *G01N 2333/5409* (2013.01); *G01N 2333/57* (2013.01); *H04L 2209/08* (2013.01); *H04L 2209/24* (2013.01)

(56) References Cited

U.S. PATENT DOCUMENTS

| | | |
|---|---|---|
| 8,774,406 B2 | 7/2014 | Choi et al. |
| 8,781,111 B2 | 7/2014 | Qi et al. |
| 9,135,453 B2 | 9/2015 | Shen-Orr et al. |
| 9,135,791 B2 * | 9/2015 | Nakamura ............... H04B 3/36 |
| 9,401,802 B2 | 7/2016 | Card |
| 9,495,111 B2 | 11/2016 | Hars et al. |
| 9,774,614 B2 | 9/2017 | Patne et al. |
| 2006/0256105 A1 | 11/2006 | Scarlata et al. |
| 2006/0256108 A1 | 11/2006 | Scarlata |
| 2008/0235756 A1 | 9/2008 | Cohen et al. |
| 2009/0010424 A1 | 1/2009 | Qi et al. |
| 2010/0166177 A1 | 7/2010 | Sirio et al. |
| 2013/0064362 A1 | 3/2013 | Tang et al. |
| 2017/0070341 A1 | 3/2017 | Teglia |
| 2017/0288855 A1 | 10/2017 | Kumar et al. |

FOREIGN PATENT DOCUMENTS

| | | |
|---|---|---|
| JP | 2006-25366 A | 1/2006 |
| JP | 2006-54568 A | 2/2006 |
| JP | 2006-81059 A | 3/2006 |

OTHER PUBLICATIONS

Communication dated Apr. 20, 2023, issued by the Korean Intellectual Property Office in Korean Application No. 10-2018-0027082.

* cited by examiner

FIG. 9

| Control value | | | Real_sub_round select condition | |
|---|---|---|---|---|
| Virtual sub_round option | LV1 | LV2 | Condition | Real : Virtual Ratio |
| 0 | { {7{1'b1}}, {1{1'b0}} } | { {7{1'b1}}, rand[0] } | | 1:1 |
| 1 | { {6{1'b1}}, {2{1'b0}} } | { {6{1'b1}}, rand[1:0] } | | 1:3 |
| 2 | { {5{1'b1}}, {3{1'b0}} } | { {5{1'b1}}, rand[2:0] } | Sub_round_cnt == Real_sub_round → Real_sub_round Sub_round_cnt != Real_sub_round → Virtual_sub_round | 1:7 |
| 3 | { {4{1'b1}}, {4{1'b0}} } | { {4{1'b1}}, rand[3:0] } | | 1:15 |
| 4 | { {3{1'b1}}, {5{1'b0}} } | { {3{1'b1}}, rand[4:0] } | | 1:31 |
| 5 | { {2{1'b1}}, {6{1'b0}} } | { {2{1'b1}}, rand[5:0] } | | 1:63 |
| 6 | { {1{1'b1}}, {7{1'b0}} } | { {1{1'b1}}, rand[6:0] } | | 1:127 |
| 7 | {8{1'b0}} | rand[7:0] | | 1:255 |

| | V_op | R_op |
|---|---|---|
| Virtual_sub_round | dummy data + dummy key | dummy data + dummy key |
| Real_sub_round | dummy data + dummy key | real data + real key |

T1

ENCRYPTION DEVICE AND OPERATION METHOD THEREOF

CROSS-REFERENCE TO RELATED APPLICATIONS

This application is a continuation application of U.S. application Ser. No. 16/157,242, filed Oct. 11, 2018, which claims priority from Korean Patent Application No. 10-2017-0134252, filed on Oct. 16, 2017, in the Korean Intellectual Property Office, and Korean Patent Application No. 10-2018-0027082, filed on Mar. 7, 2018, in the Korean Intellectual Property Office, the disclosures of each of which are incorporated by reference herein in their entireties.

BACKGROUND

Apparatuses, devices, and methods consistent with the present disclosure relate to an encryption device and a method of operating the same, and more particularly, to an encryption device for randomly performing a virtual operation and a method of operating the encryption device.

Smart cards and integrated circuit (IC) cards include security information of users. In order to prevent leakage of the security information by hacking, etc., there is a need for encryption/decryption devices for encrypting and transmitting security information transmitted through signature and authorization.

One of the important factors to realize encryption/decryption devices is to apply a method of preventing side channel analysis (SCA). A method of randomly or uniformly propagating power and electromagnetic waves that are information collected through a side channel may be used as the above method.

SUMMARY

It is an aspect to provide an encryption device and a method of operating the same for randomly performing a virtual operation and a real operation and a method of operating the encryption device.

According to an aspect of an example embodiment, there is provided a method of operating an encryption device for performing a real operation and a virtual operation, the method including performing a virtual operation: when a real operation request signal is received, determining whether the virtual operation being performed is completed; and in response to the virtual operation being completed, performing a real operation in response to the real operation request signal.

According to another aspect of an example embodiment, there is provided a method of operating an encryption device for performing a virtual operation and a real operation, each of which includes a plurality of round operations each including a plurality of sub-round operations classified into real sub-round operations and virtual sub-round operations, the method including initializing a count value and a random value regarding the plurality of sub-round operations and starting forming a round comprising a plurality of sub-round operations including one real sub-round operation and a plurality of virtual sub-round operations: deriving a count value by counting the sub-round operations: performing the one real sub-round operation when the count value is equal to the random value, and performing one of the plurality of virtual sub-round operations when the count value is different from the random value; and when the count value is equal to a reference count value, completing the round.

According to another aspect of an example embodiment, there is provided an encryption device for performing a virtual operation and a real operation each including a plurality of round operations each including a plurality of sub-round operations classified into real sub-round operations and virtual sub-round operations, the encryption device including: a first virtual operation register configured to store first dummy data and a first dummy encryption key on which the virtual sub-round operations are based: a second virtual operation register configured to store second dummy data and a second dummy encryption key on which the virtual sub-round operations are based; and a first multiplexer configured to receive a first output from the first virtual operation register and a second output from the second virtual operation register, select one of the first output or the second output based on a random bit, and output the one of the first output or the second output that is selected.

BRIEF DESCRIPTION OF THE DRAWINGS

Example embodiments will be more clearly understood from the following detailed description taken in conjunction with the accompanying drawings in which:

FIG. 9 is a table showing an example of options that may be set when a round formation operation is performed, according to an example embodiment:

DETAILED DESCRIPTION

Hereinafter, one or more example embodiments will be described in detail with reference to the attached drawings.

Figure 1:
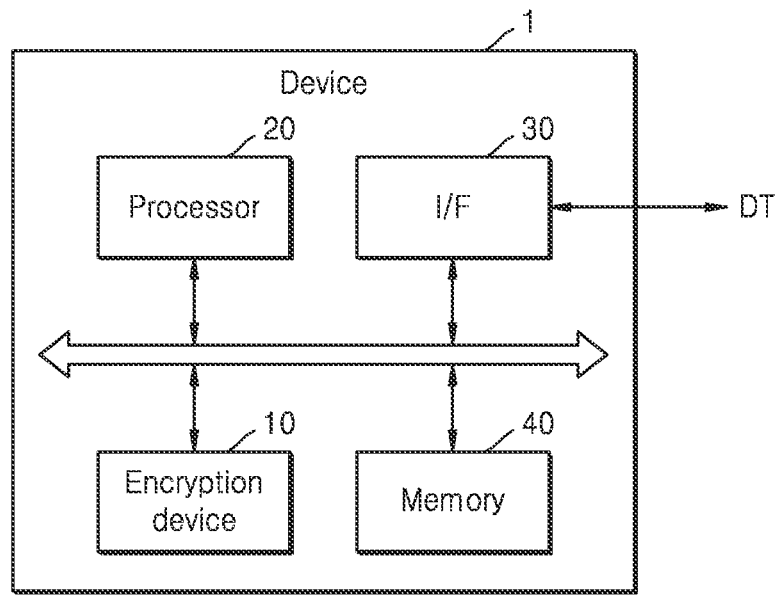
FIG. 1 is a block diagram of a device according to an example embodiment.

FIG. 1 is a block diagram of a device 1 according to an example embodiment.

Referring to FIG. 1, the device 1 may include an encryption device 10, a processor 20, an interface (I/F) 30, and a memory 40. The device 1 may transceive data DT with an external device. For example, the device 1 may transceive the data DT with a smart card, a memory card, or another device.

The processor 20 may transceive the data DT with one or more other devices located outside of the device 1 through the I/F 30. The processor 20 may perform tasks and may store task results in the memory 40. For example, the processor 20 may include multiple cores.

The memory 40 may store various types of data for operation of the processor 20. The memory 40 may be embodied as, for example, Dynamic Random Access Memory (DRAM), Mobile DRAM, Static RAM (SRAM), Phase change RAM (PRAM), Ferroelectric RAM (FRAM), Resistive RAM (RRAM or ReRAM), and/or Magnetic RAM (MRAM).

The encryption device 10 may perform encryption and/or decryption on the data DT received from outside of the device 1. The encryption device 10 may maintain the security of the data DT by performing an encryption operation based on an encryption algorithm. The encryption algorithm may be, for example, an algorithm for generating data encrypted by using an encryption key. The encryption algorithm may include various algorithms such as a Message-Digest algorithm (MD5), a Secure Hash Algorithm (SHA), Rivest Shamir Adleman (RSA), an Advanced Encryption Standard (AES), and a Data Encryption Standard (DES).

The encryption device 10 according to an example embodiment may perform a real operation for an encryption operation and a virtual operation irrelevant to the real operation. The real operation and the virtual operation may include a real round operation and a virtual round operation, respectively. In the present specification, the real operation and the virtual operation may be encryption/decryption operations including round operations (real round operations or virtual round operations). In an example embodiment, one virtual round operation and one real round operation may each include sub-round operations. For example, the sub-round operations may be classified into real sub-round operations and virtual sub-round operations.

In an example embodiment, one round of the virtual operation and one round of the real operation may each include one real sub-round operation and a plurality of virtual sub-round operations of a first number. That is, one round of the virtual operation may include one real sub-round operation and a plurality of virtual sub-round operations of a first number, and one round of the real operation may include one real sub-round operation and a plurality of virtual sub-round operations of the first number. For example, an order of performing the real sub-round operation and the virtual sub-round operations in one round may be randomly changed. In an example embodiment, a sum of the number of real sub-round operations and the number of virtual sub-round operations, both of which are included in one round, may be 2 raised to a power. In other words, a value obtained by adding '1' to the first number may be 2 raised to a power.

Figure 2:
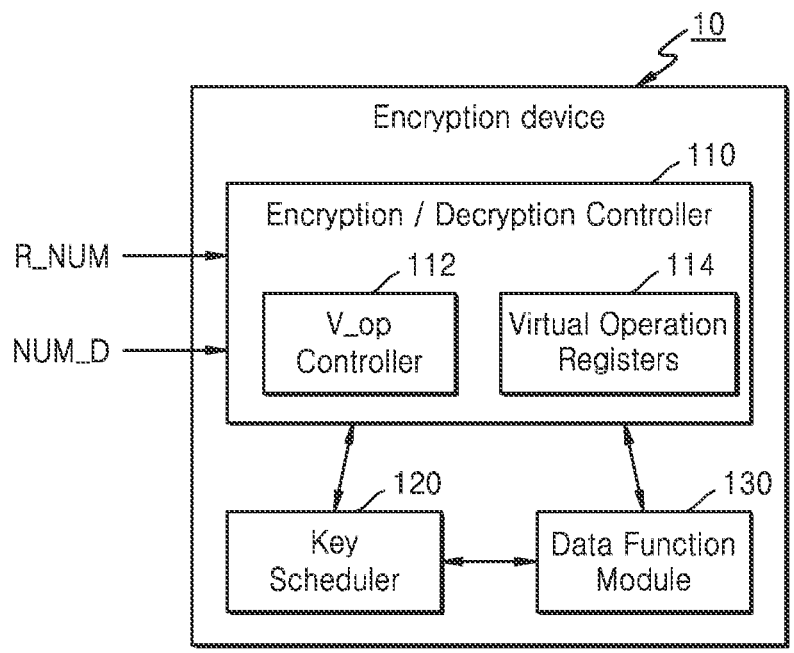
FIG. 2 is a detailed block diagram of an encryption device according to an example embodiment.

FIG. 2 is a detailed block diagram of an encryption device according to an example embodiment. For example, FIG. 2 may be a detailed block diagram of the encryption device 10 of FIG. 1.

Referring to FIG. 2, the encryption device 10 may include an encryption/decryption controller 110, a key scheduler 120, and a data function module 130. The encryption/decryption controller 110 may control overall operations of the encryption device 10. The encryption/decryption controller 110 may include a virtual operation (V-op) controller 112 and virtual operation (V_op) registers 114.

In an example embodiment, when a real operation is requested, the virtual operation controller 112 may control the number of virtual operations to be performed before the real operation is performed based on a delay number NUM_D indicating a number of delays that is received from the outside of the encryption device 10. For example, when the real operation is requested while the virtual operation is performed on the data function module 130, the virtual operation controller 112 may control the data function module 130 in such a manner that the virtual operations are performed by as many as the delay number NUM_D and then the real operation is performed.

For example, the delay number NUM_D may be a value that is received from a host (not illustrated) outside the encryption device 10. As another example, the virtual operation controller 112 may control the number of virtual operations to be performed before the real operation is performed, based on a random value R_NUM received from a random number generator located outside of the encryption device 10.

In an example embodiment, the virtual operation registers 114 may each store a pair of data and an encryption key for a virtual sub-round operation. For example, each virtual operation register 114 may include a first virtual operation register and a second virtual operation register, and each of the first and second virtual operation registers may store a pair of dummy data and a dummy encryption key.

In an example embodiment, based on certain random bits included in the random value R_NUM, one of the first virtual operation register and the second virtual operation register may be selected. One virtual sub-round operation may be performed based on the dummy data and the dummy encryption key which are stored in the selected one of the first virtual operation register and the second virtual operation register. That is, whenever virtual sub-round operations are performed, one of the first virtual operation register and the second virtual operation register may be selected. However, the above description is merely an example, and the number of virtual operation registers 114 is not limited thereto.

The key scheduler 120 may process an encryption key for each sub-round operation. In an example embodiment, the key scheduler 120 may receive an encryption key stored in a register and may perform a bit-shift operation on the encryption key received based on a rule that is set for each sub-round operation. The rule may be previously set. The register for storing the encryption key may be the virtual operation register 114, or a real operation register (not illustrated). After the encryption key is processed by performing the bit-shift operation, the key scheduler 120 may provide the processed encryption key to the data function module 130. Also, the key scheduler 120 may update the processed encryption key to the register that provided the encryption key before processing the same.

The data function module 130 may perform an encryption operation on the data DT that is input based on the encryption key. The data function module 130 may perform an encryption operation by performing, for example, a permutation whereby locations of bits of the data DT are mixed based on the encryption key. Alternatively or additionally, the data function module 130 may perform the encryption operation by performing a substitution whereby the data is substituted with other mapped data, based on the encryption key. The data function module 130 may update, to the register, the data DT on which the encryption operation is performed. An operation performed by the data function module 130 may be determined as one of a real sub-round operation and a virtual sub-round operation, depending on the data DT and a type of the encryption key.

In an example embodiment, when the data function module 130 performs the encryption operation based on real data and a real encryption key, the encryption operation may be determined as a real sub-round operation. Alternatively, when the data function module 130 performs the encryption operation based on the dummy data and the dummy encryption key, the encryption operation may be determined as a virtual sub-round operation. However, the example embodiments are not limited thereto. When the data function module 130 performs the encryption operation based on the dummy data and the real encryption key, or based on the real data and the dummy encryption key, the encryption operation may be determined as a virtual sub-round operation.

In an example embodiment, when a real operation request signal is received by the encryption/decryption controller 110 while the virtual operation is performed by the data function module 130, the data function module 130 may not stop and may continue to perform the virtual operation, which was in the process of being performed when the real operation request signal was received, thereby completing the virtual operation. In other words, the data function module 130 may perform all round operations included in the virtual operation, which was in the process of being performed when the real operation request signal was received, thereby completing the round operations before performing the real operation requested by the real operation request signal.

Figure 3:
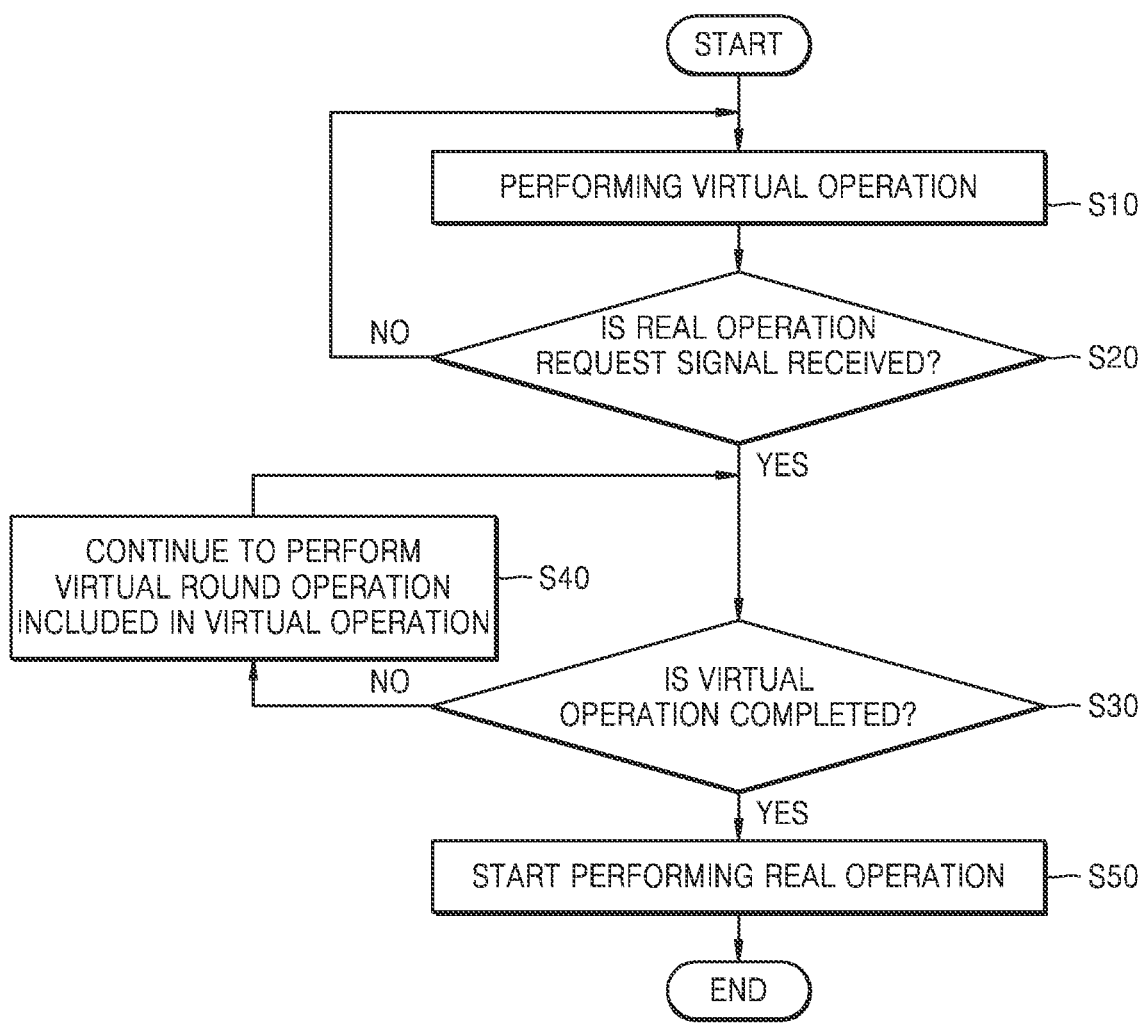
FIG. 3 is a flowchart of a method of operating an encryption device, according to an example embodiment.

FIG. 3 is a flowchart of a method of operating an encryption device, according to an example embodiment. For example, FIG. 3 may be a flowchart of operations of the encryption device 10 of FIG. 2. Hereinafter, the flowchart of FIG. 3 will be described with reference to FIG. 2.

Referring to FIG. 3, in operation S10, the encryption device 10 may start performing a virtual operation. In an example embodiment, a virtual operation in one unit may include plural round operations. Each round operation may be, for example, either a real round operation or a virtual round operation. The virtual operation may be performed by, for example, the data function module 130.

Then, in operation S20, the encryption device 10 may determine whether the real operation request signal is received. When the real operation request signal is not received (S20, NO), the encryption device 10 may continue to perform the virtual operation. For example, the encryption device 10 may complete the virtual operation currently being performed and may start performing a new virtual operation.

On the other hand, when the real operation request signal is received (S20, YES), the encryption device 10 may determine whether the virtual operation that is currently being performed is completed. When it is determined that the virtual operation is not completed (S30, NO), the encryption device 10 may continue to perform a virtual round operation included in the virtual operation, in operation S40. Otherwise, when it is determined that the virtual operation is completed (S30, YES), the encryption device 10 may then start performing the real operation, in operation S50.

According to an example embodiment, although the real operation request signal is received, since the encryption device 10 may not immediately perform the real operation and may continue to perform the virtual operation to complete the same, a real operation part is not specified despite a side channel attack on the encryption device 10, for example, power waveform analysis of an attacker. That is, a real operation is not immediately started in response to the real operation request signal thus confusing a side channel attack on the encryption device 10. Accordingly, the encryption device 10 may have an enhanced defense function with respect to the side channel attack.

Figure 4:
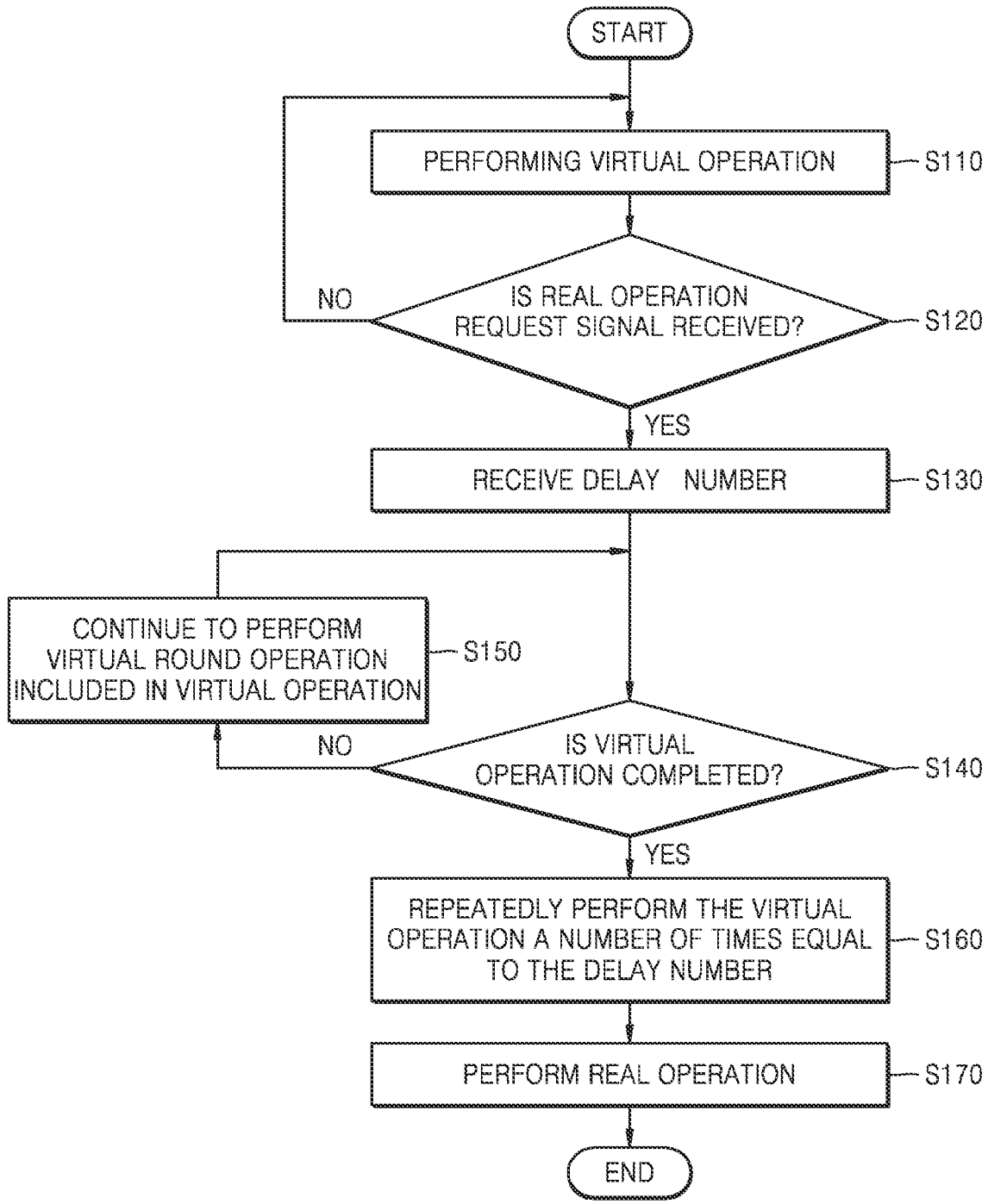
FIG. 4 is a flowchart of a method of operating an encryption device, according to an example embodiment.

FIG. 4 is a flowchart of a method of operating an encryption device, according to an example embodiment. For example, FIG. 4 may be a flowchart of operations of the encryption device 10 of FIG. 2. The descriptions already provided with reference to FIG. 3 will not be repeated herein.

Referring to FIG. 4, the encryption device 10 may perform a virtual operation in operation S110 and may determine whether a real operation request signal is received while the virtual operation is performed in operation S120. When the real operation request signal is not received (S120, NO), the encryption device 10 may continue to perform the virtual operation.

When the real operation request signal is received (S120, YES), the encryption device 10 may receive a delay number NUM_D indicating a number of delays in operation S130. For example, the delay number NUM_D may be a value received from a host (not illustrated) outside the encryption device 10, or may be a random value received from a random value generator (not illustrated) outside the encryption device 10. The random value may be generated by, for example, a Linear Feedback Shift Register (LFSR) or a Random Number Generator (RNG) outside the encryption device 10.

After receiving the delay number, the encryption device 10 may determine whether the virtual operation is completed, in operation S140. When it is determined that the virtual operation is not completed (S140, NO), the encryption device 10 may continue to perform a virtual round operation included in the virtual operation, in operation S150.

Otherwise, when it is determined that the virtual operation is completed (S140, YES), the encryption device 10 may repeatedly perform the virtual operation a number of times equal to the delay number NUM_D, in operation S160. For example, when the delay number NUM_D indicating the number of delays is equal to N (where, N is a natural number equal to or greater than 1), the encryption device 10 may perform virtual operations N-1 times in addition to the virtual operation that was being performed when the real operation request signal was received. However, the example embodiments are not limited thereto. When the delay number NUM_D is equal to N, the encryption device 10 may perform virtual operations N times except the virtual operation that was being performed when the real operation request signal was received. That is, the delay number may include or not include the virtual operation that was being performed when the real operation request signal was received. As another example, the encryption device 10 may control the number of times that the virtual operations are to be performed before the real operation is performed, in operation S170, based on the random value R_NUM received from the outside.

In the present example embodiment, it has been described that the encryption device 10 receives the real operation request signal in operation S120 and then receives the delay number NUM_D indicating the number of delays in operation S130l. However, the example embodiments are not limited thereto. That is, the encryption device 10 may receive the delay number at any time, for example, while the virtual operation is being performed or before performing the virtual operation.

According to an example embodiment, although the real operation request signal is received, the real operation is not immediately performed, and after the virtual operations are further repeatedly performed by as many times as the delay number NUM_D, the real operation is performed. Thus, a real operation part is not specified despite a side channel attack on the encryption device 10. Accordingly, the encryption device 10 may have an enhanced defense function with respect to the side channel attack.

Figure 5:
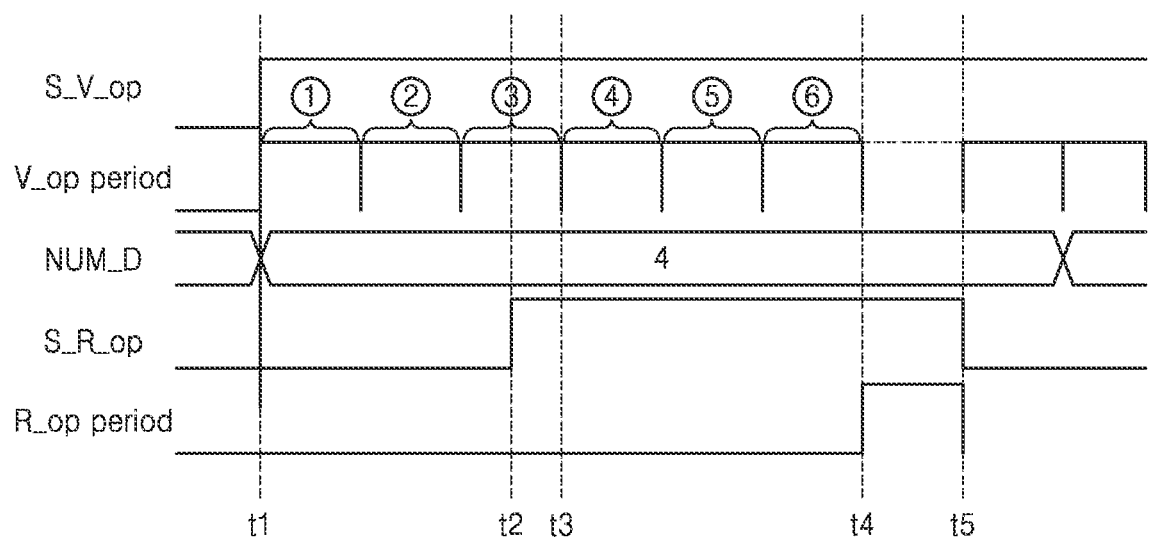
FIG. 5 is a timing diagram for explaining operations of an encryption device, according to an example embodiment.

FIG. 5 is a timing diagram for explaining each operation of an encryption device, according to an example embodiment. For example, FIG. 5 may be a timing diagram for explaining operations of the encryption device 10 of FIG. 2. Hereinafter, the timing diagram of FIG. 5 will be described with reference to FIG. 2.

Referring to FIG. 5, a virtual operation request signal S_V_op may be activated at a first point in time t1. For example, when an option of performing a virtual operation of the encryption device 10 is turned on, the encryption device 10 may be reset, and the virtual operation request signal S_V_op may be activated. As another example, when the option of performing the virtual operation of the encryption device 10 is turned off, the option of performing the virtual operation of the encryption device 10 is turned on, and the virtual operation request signal S_V_op may be activated.

The virtual operation may be performed based on the activated virtual operation request signal S_V_op. Also, at the first point in time t1, the encryption device 10 may receive the delay number NUM_D indicating the number of delays. In the present example embodiment shown in FIG. 5, it is described that each signal is activated in a logic-high state. However, example embodiments are not limited thereto, and the signals may be activated in the logic-low state. In addition, in the present example embodiment, the delay number NUM_D is equal to '4', but this is merely an example for convenience of explanation, and the example embodiments are not limited thereto.

A first virtual operation ((1) and a second virtual operation (2) may be performed in response to the virtual operation request signal S_V_op. While a third virtual operation (3) is performed in response to the virtual operation request signal S_V_op, a real operation request signal S_R_op may be activated at a second point in time t2. In an example embodiment, the encryption device 10 may not stop and may continue to perform the third virtual operation (3) at the second point in time t2, thereby completing the third virtual operation (3). That is, the encryption device 10 may perform all round operations included in the third virtual operation (3) and may complete the third virtual operation (3) by a third point in time t3.

In an example embodiment, the encryption device 10 may further perform virtual operations, e.g., a fourth virtual operation (4), a fifth virtual operation (5), and a sixth virtual operation (6) shown in FIG. 5, three times after the third point in time t3. That is, since the delay number NUM_D is equal to '4' and the third virtual operation (3) is completed by the third point in time t3 after the real operation request signal S_R_op is activated, the encryption device 10 may further perform the other virtual operations (the fourth to sixth virtual operations 4 to 6) three times. However, the example embodiments are not limited thereto. The encryption device 10 may not count a virtual operation, which is completed at the third point in time t3, and may further perform virtual operations four times.

Additional virtual operations may be completed by a fourth point in time t4, and a real operation may be performed. The real operation may be performed from the fourth point in time t4 to a fifth point in time t5, and the real operation request signal S_R_op may be inactivated at the fifth point in time t5.

Figure 6:
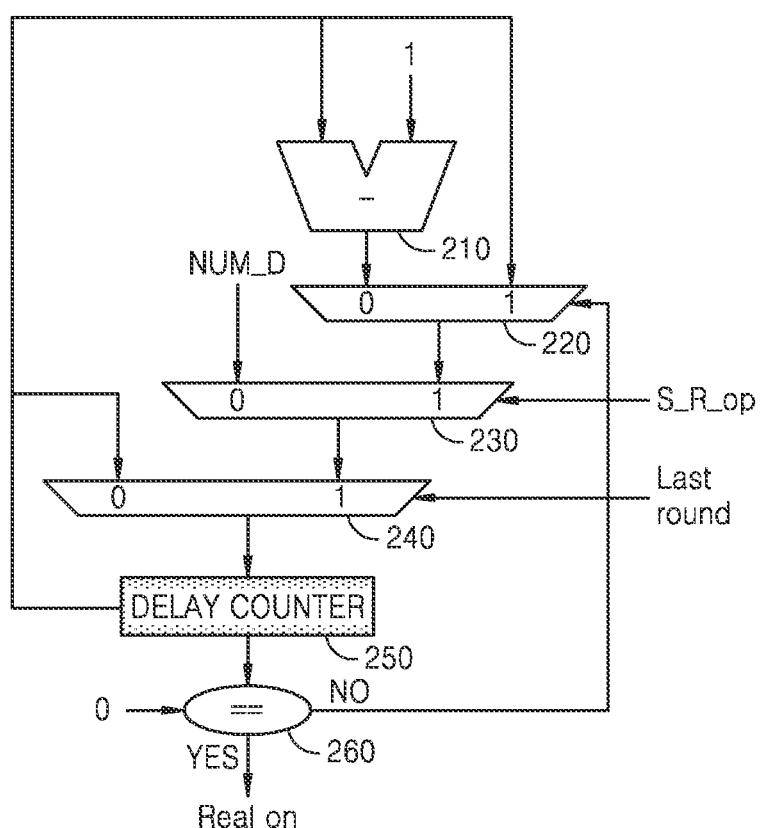
FIG. 6 is a diagram illustrating part of an encryption device for performing an encryption operation, according to an example embodiment.

FIG. 6 is a diagram illustrating part of an encryption device for performing an encryption operation, according to an example embodiment. For example, FIG. 6 may illustrate an example of a logic circuit structure for performing the operations of FIG. 4. For example, the logic circuit structure of FIG. 6 may be included in the virtual operation controller 112 of FIG. 2.

Referring to FIG. 6, the encryption device 10 may include a logic circuit including a subtractor 210, a first multiplexer 220, a second multiplexer 230, and a third multiplexer 240, a delay counter 250, and a comparator 260 so as to perform the operations of FIG. 4. Based on an output from the comparator 260, the first multiplexer 220 may select, as an output value, a value input from the subtractor 210 or a value input from the delay counter 250. For example, in a case in which the comparator 260 determines that a counting value of the delay counter 250 is not equal to '0', the first multiplexer 220 may select, as an output value, the value input from the subtractor 210.

The second multiplexer 230 may select, as an output value, either the delay number or the value input from the first multiplexer 220, in response to the real operation request signal S_R_op. For example, in a case in which the real operation request signal S_R_op is activated, the second multiplexer 230 may select the value input from the first multiplexer 220 as the output value.

The third multiplexer 240 may select, as an output value, a value input from the delay counter 250 or a value input from the second multiplexer 230, in response to a last round signal. For example, the last round signal may be a signal activated during a last round operation included in either the virtual operation or the real operation. In a case in which the last round signal is activated, the third multiplexer 240 may select the value input from the second multiplexer 230 as the output value.

While the virtual operation is performed, when the real operation request signal S_R_op is activated and the comparator 260 determines that the counting value of the delay counter 250 is not equal to '0', the first multiplexer 220 may be set to select the value input from the subtractor 210 as the output value, and the second multiplexer 230 may be set to select the value input from the first multiplexer 220 as the output value. Also, the third multiplexer 240 may be set to select the value input from the second multiplexer 230 as the output value, based on the last round signal.

Accordingly, when the real operation request signal S_R_op is activated, the delay counter 250 may perform counting by subtracting '1' each time from the delay number NUM_D. The comparator 260 may determine whether the value output from the delay counter 250 is equal to 0, and when the value output from the delay counter 250 is equal to 0, a signal may be output to perform the real operation. Also, since the third multiplexer 240 selects the output value based on whether the last round signal is activated, when the delay number NUM_D is equal to '0', although the real operation request signal S_R_op is activated, the encryption device 10 may finish performing a last round operation of the virtual operation having been performed and then may perform a next real operation.

Figure 7:
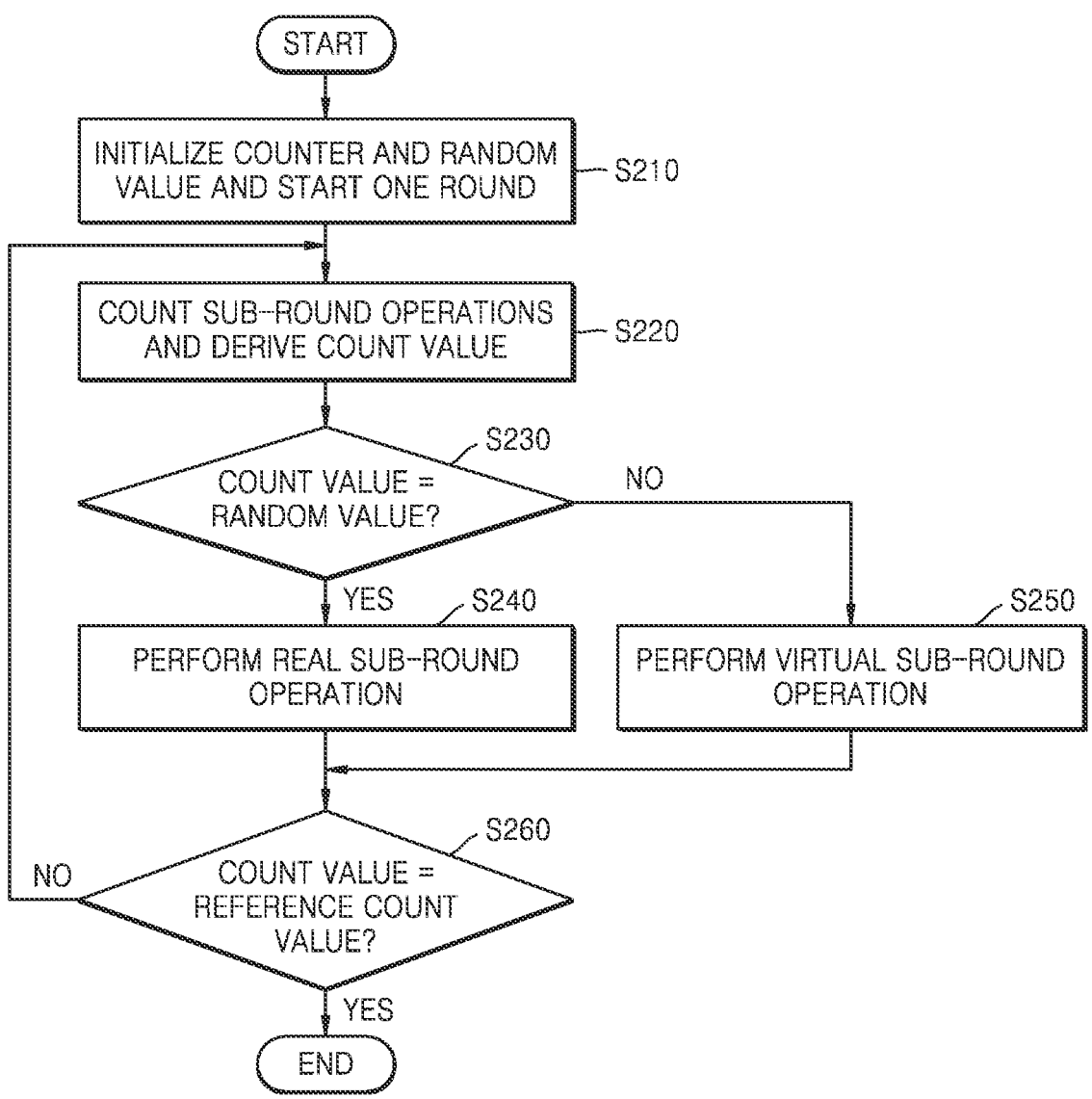
FIG. 7 is a flowchart of a round formation operation of an encryption device, according to an example embodiment.

FIG. 7 is a flowchart of a round formation operation of an encryption device, according to an example embodiment. For example, FIG. 7 may be a flowchart of operations of the encryption device 10 of FIG. 2. Hereinafter, the flowchart of FIG. 7 will be described with reference to FIG. 2.

Referring to FIG. 7, in operation S210, the encryption device 10 may initialize a counter and a random value and may start one round. The counter may count sub-round operations that are sequentially performed. The random value may be a value that becomes a basis of a point in time when a real sub-round operation is performed in one round. For example, the random value may be stored in a register. In an example embodiment, the encryption device 10 may store, in the register, the random value R_NUM input from the outside of the encryption device 10 as an initialization value.

In operation S220, the encryption device 10 may count sub-round operations by using the counter and may derive a count value. In operation S230, the encryption device 10 may determine whether the derived count value is equal to an initialized random value. For example, the comparator may compare the count value with the random value and determine whether the output count value is equal to the random value.

When the count value is equal to the random value (S230, YES), the encryption device 10 may perform a real sub-round operation, in operation S240. Otherwise, when the count value is different from the random value (S230, NO), the encryption device 10 may perform a virtual sub-round operation in operation S250.

In operation S260, a determination as to whether the derived count value is equal to a reference count value may be made. The reference count value may be set in advance. In an example embodiment, the reference count value may be a max count value. The max count value may be, for example, the number of sub-round operations to be included in one round. In an example embodiment, the max count value may be 'a value obtained by subtracting 1 from 2 raised to a power'. For example, the comparator may compare the count value with the reference count value and determine whether the output count value is equal to the reference count value.

When the count value is equal to the reference count value (S260, YES), the encryption device 10 may complete one round. Otherwise, when the count value is different from the reference count value (S260, NO), the encryption device 10 may return to operation S220 again.

Figure 8:
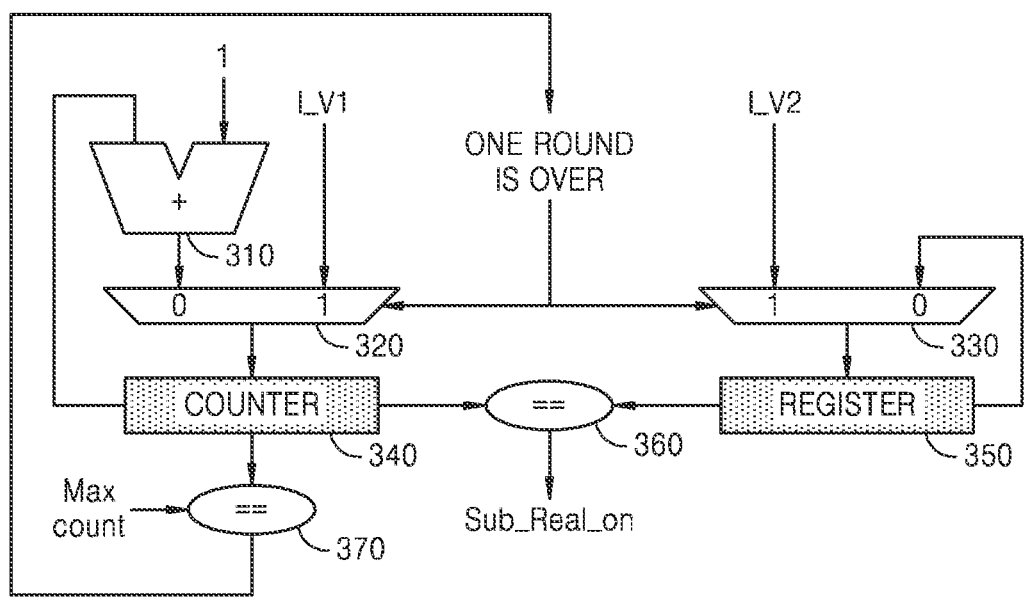
FIG. 8 is a diagram illustrating part of an encryption device for a round formation operation, according to an example embodiment.

FIG. 8 is a diagram illustrating part of an encryption device for a round formation operation, according to an example embodiment. For example, FIG. 8 may illustrate an example of a logic circuit structure for performing the operation of FIG. 7. For example, the logic circuit structure of FIG. 8 may be included in the virtual operation controller 112 of FIG. 2.

Referring to FIG. 8, the encryption device 10 may include a logic circuit including an adder 310, a first multiplexer 320 and a second multiplexer 330, a counter 340, a register 350, and a first comparator 360 and a second comparator 370 for the round formation operation. In an example embodiment, the counter 340 may count sub-round operations that are sequentially performed, and except that an initial value is input, the counter 340 may increase the number of counts by 1.

The counter 340 may perform initialization when a count value has a maximum value. For example, when the count value is expressed as binary numbers of 8 bits, the maximum value may be 2'b1111_1111. For example, an initial value I_V1 of the counter 340 may be a value obtained by subtracting, from the maximum value, the number of times that a real sub-round operation and a virtual sub-round operation included in one round are performed. The second comparator 370 may compare a max count value with a count value of the counter 340 and may output a signal indicating that one round ends, based on whether two values, that is, the max count value and the count value, are equal to each other.

The register 350 may store a random value that is a basis of performance of the real sub-round operation. For example, the random value may form at least some bits among bits that form an initial value I_V2. The register 350 may perform initialization of the random value by inputting the initial value I_V2. For example, the initial value I_V2 may be the random value R_NUM that is received from the outside of the encryption device 10.

The first comparator 360 may compare the count value of the counter 340 with the random value stored in the register 350. For example, when the count value of the counter 340 is equal to the random value stored in the register 350, the first comparator 360 may output a real sub-round operation performance signal Sub_Real_on. Accordingly, a point in time when the read sub-round operation is performed in one round may be randomly determined.

FIG. 9 is a table showing examples of respective options that may be set during the round formation operation, according to an example embodiment. For example, FIG. 9 shows that the round formation operations described with reference to FIGS. 7 and 8 are performed based on 8 bits. However, this is merely an example for convenience of explanation, and the example embodiments are not limited thereto. Hereinafter, the table of FIG. 9 will be described with reference to FIG. 8.

Referring to FIG. 9, based on 8 bits, the initial value I_V1 of the counter 340 may be expressed as eight different bits. Also, the initial value I_V2 of the random value, which is input to the register 350, may correspond to the initial value I_V1 of the counter 340 and may be expressed as eight different bits. In a bit formation of the initial value I_V2, 'rand [ ]' may be a random function. In the present example shown in FIG. 9, each of the initial values I_V1 and I_V2 is written in a hardware technology language such as Verilog. However, this is merely an example for convenience of explanation, and the example embodiments are not limited thereto.

In an example embodiment, a ratio of performing real sub-round operations and virtual sub-round operations included in one round may be set as an option. For example, when a virtual sub-round operation option is given as n (where, n is an integer equal to or greater than 0), a sum of the number of real sub-round operations and the number of virtual sub-round operations may be set to be 2n+1. That is, when one real sub-round operation and virtual sub-round operations are performed in one round, and when the virtual sub-round operation option is given as n, the number of times that the virtual sub-round operations are performed may be set to be 2n+1-1.

According to an example embodiment, the encryption device 10 may set, as an option, a ratio of performing the real sub-round operation and the virtual sub-round operations included in one round, and thus may implement a round formation operation by using a simple logic in a binary register structure.

Figure 10:
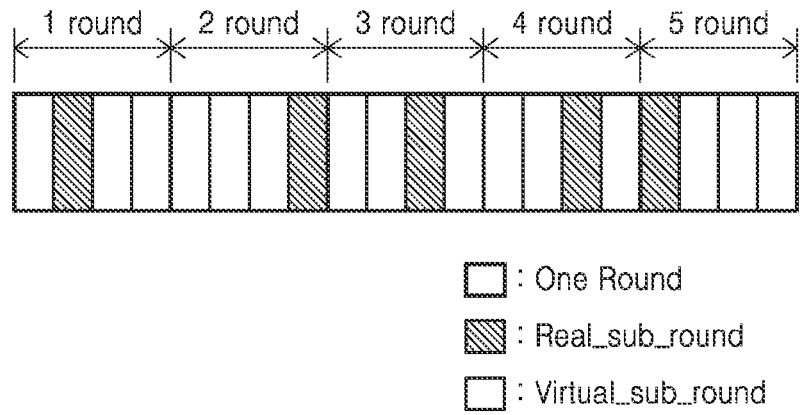
FIG. 10 is a conceptual view of an example in which multiple rounds are performed when the rounds are formed, according to an example embodiment.

FIG. 10 is a conceptual view of an example of performing rounds when the rounds are formed, according to an example embodiment. For example, FIG. 10 illustrates an example of a result of the round formation operations of FIGS. 7 and 8.

Referring to FIG. 10, an encryption operation including five round operations is performed. For example, the encryption operation may be the real operation or the virtual operation described with reference to FIG. 5. FIG. 10 may illustrate that a real sub-round operation and virtual sub-round operations included in each round are performed at a ratio of 1:3. That is, in each of the five round operations, one real sub-round operation and three virtual sub-round operations may be randomly performed. In each round operation, points in time when the virtual sub-round operations are performed may be determined based on random bits included in the initial value I_V2. Accordingly, when the encryption operation is performed, randomness of the real sub-round operation may be secured, and the real sub-round operations may be evenly performed.

Figure 11:
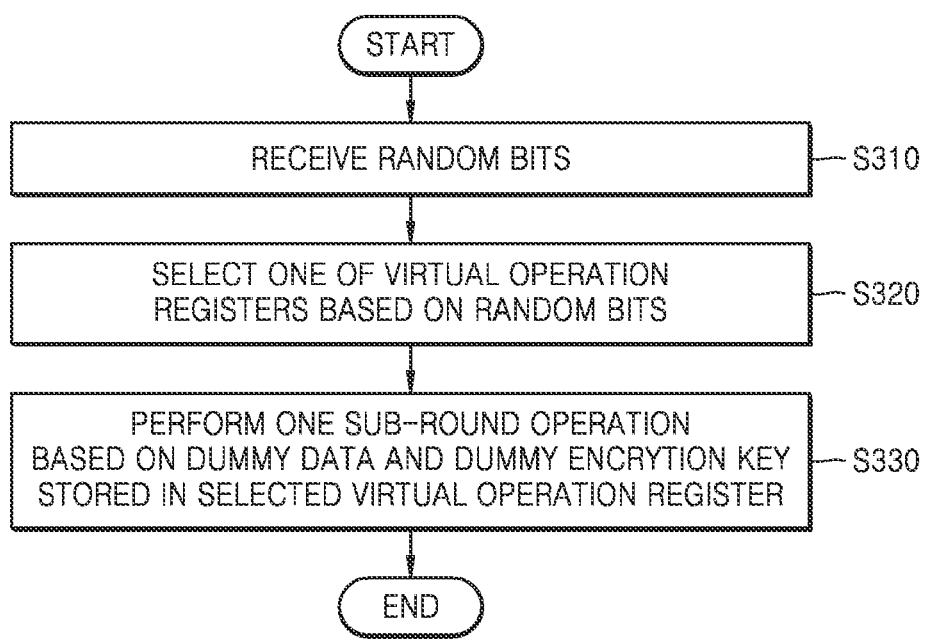
FIG. 11 is a flowchart of a method of operating an encryption device, according to an example embodiment.

FIG. 11 is a flowchart of a method of operating an encryption device, according to an example embodiment. For example, FIG. 11 may be a flowchart of operations of the encryption device 10 of FIG. 2. Hereinafter, the flowchart of FIG. 11 will be described with reference to FIG. 2.

Referring to FIG. 11, in operation S310, the encryption device 10 may receive random bits. For example, based on the random bits, one of the virtual operation registers 114 may be selected. In an example embodiment, the random bits may be included in the random value R_NUM received from the outside of the encryption device 10. The random bits may be generated by, for example, an LFSR or an RNG outside the encryption device 10 as discussed above.

In operation S320, the encryption device 10 may select one of the virtual operation registers 114 based on the random bits. For example, selection of one of the virtual operation registers 114 may be performed by a multiplexer operating based on the random bits. In an example embodiment, each virtual operation register 114 may store a pair of the dummy data and the dummy encryption key for the virtual sub-round operations. In operation S330, the encryption device 10 may perform one sub-round operation based on the dummy data and the dummy encryption key stored in the selected virtual operation register 114.

Figures 12, 13:
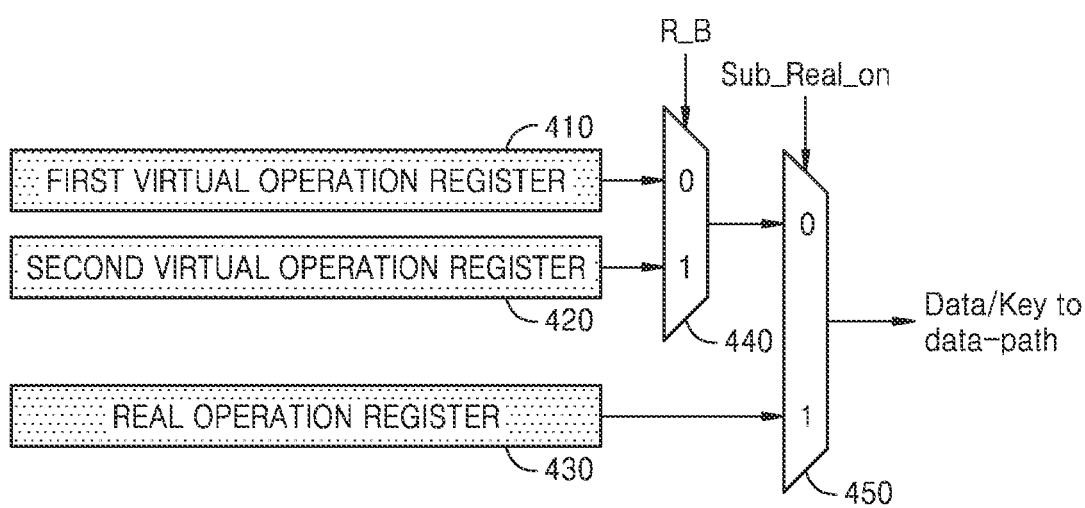
FIG. 12 is a table for explaining operation of an encryption device, according to an example embodiment.
FIG. 13 is a diagram of part of an encryption device for performing an encryption operation, according to an example embodiment.

FIG. 12 is a table for explaining operation of an encryption device, according to an example embodiment.

Referring to FIG. 12, in the table TI, combinations of a virtual operation V_op, a real operation R_op, a virtual sub-round operation Virtual_sub_round, and a real sub-round operation Real_sub_round are shown. In detail, in one virtual operation V_op, the virtual sub-round operation Virtual_sub_round and the real sub-round operation Real_sub_round may be performed. Also, in one real operation R_op, the virtual sub-round operation Virtual_sub_round and the real sub-round operation Real_sub_round may be performed.

In an example embodiment, in one virtual operation V_op, an encryption operation may be performed based on a pair of dummy data and a dummy encryption key, regardless of whether the sub-round operation is the virtual sub-round operation Virtual_sub_round or the real sub-round operation Real_sub_round. As another example, in one virtual operation V_op, the encryption operation may be performed based on a pair of the dummy data and a real encryption key or a pair of real data and the dummy encryption key.

In an example embodiment, in one real operation R_op, in the case of the virtual sub-round operation Virtual_sub_round, the encryption operation may be performed based on the pair of the dummy data and the dummy encryption key.

As another example, in one real operation R_op, in the case of the virtual sub-round operation Virtual_sub_round, the encryption operation may be performed based on the pair of the dummy data and the real encryption key or the pair of the real data and the dummy encryption key.

In an example embodiment, in one real operation R_op, in the case of the real sub-round operation Real_sub_round, the encryption operation may be performed based on the pair of the real data and the real encryption key. In other words, in one real operation R_op, the encryption operation based on the real data and the real encryption key may be the real sub-round operation Real_sub_round in the real operation R_op.

FIG. 13 is a diagram of part of an encryption device for performing an encryption operation, according to an example embodiment. For example, FIG. 13 may illustrate an example of a logic circuit structure for implementing the operations of FIG. 11. For example, the logic circuit structure of FIG. 13 may be included in the virtual operation registers 114 of FIG. 2.

Referring to FIG. 13, the encryption device 10 may include a logic circuit including a first virtual operation register 410, a second virtual operation register 420, a real operation register 430, and a first multiplexer 440 and a second multiplexer 450 so as to implement the operations of FIG. 11. In the present embodiment, there are two virtual operation registers. However, one or more embodiments are not limited thereto.

The first virtual operation register 410 may store first dummy data and a first dummy encryption key (Dummy Data/Key 1). The second virtual operation register 420 may store second dummy data and a second dummy encryption key (Dummy Data/Key 2).

The first multiplexer 440 may receive a pair of the first dummy data and the first dummy encryption key from the first virtual operation register 410 and may receive a pair of the second dummy data and the second dummy encryption key from the second virtual operation register 420. The first multiplexer 440 may further receive random bits R_B and may selectively receive one of the pair of the first dummy data and the first dummy encryption key and the pair of the second dummy data and the second dummy encryption key, based on the random bits R_B. The selection of the first multiplexer 440 may be performed in each virtual sub-round operation. Accordingly, even when the virtual sub-round operations are continuously performed, the encryption device 10 may randomly perform switching of registers for data/encryption keys.

The second multiplexer 450 may select one of an output from the first multiplexer 440 and an output (i.e. Real Data/Key) from the real operation register 430 and may output the selected output, in response to the real sub-round operation performance signal Sub_Real_on. Since the encryption device 10 according to an example embodiment may randomly perform the switching of the registers regardless of whether continuous sub-round operations are virtual sub-round operations or real sub-round operations, a real operation part is not specified despite a side channel attack, in particular, power waveform analysis. Accordingly, the encryption device 10 may have an enhanced defense function with respect to the side channel attack.

Figure 14:
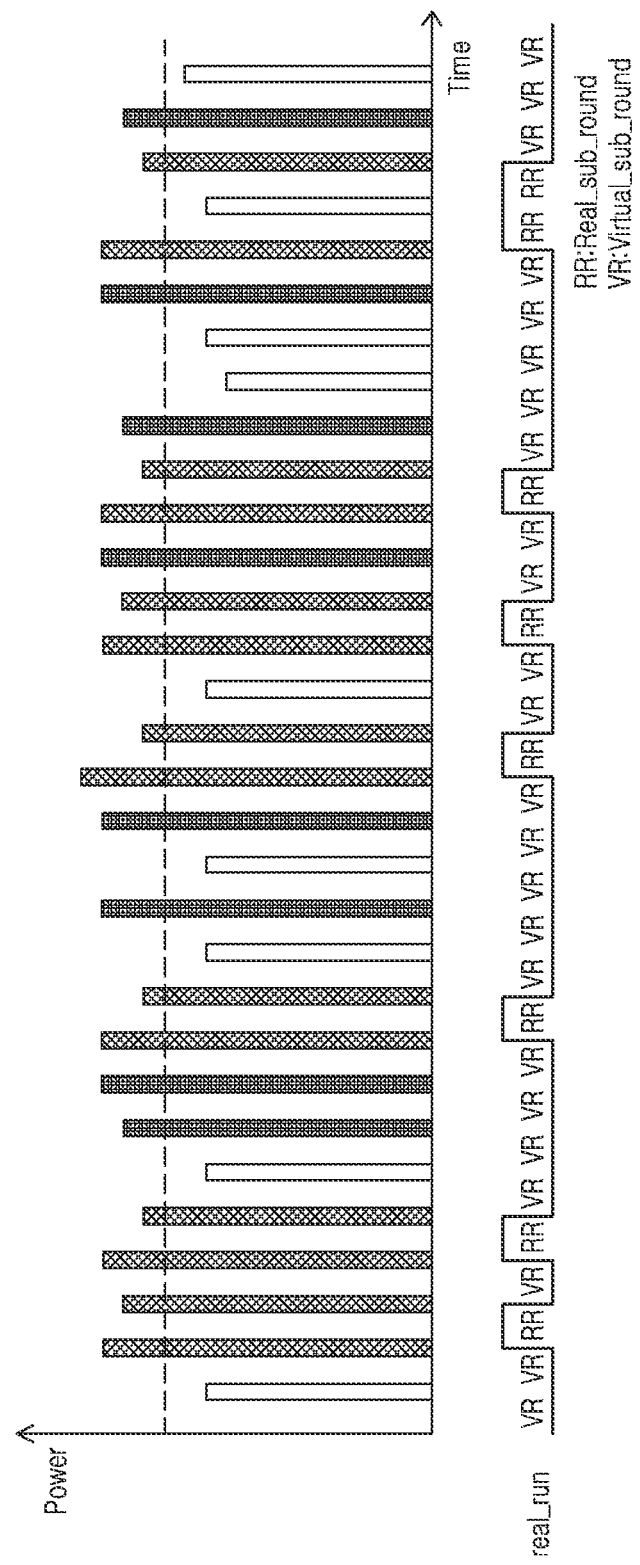
FIG. 14 is a graph showing power waveforms according to operation of an encryption device, according to an example embodiment.

FIG. 14 is a graph showing power waveforms according to operations of an encryption device, according to an example embodiment. In particular, the graph of FIG. 14 shows transition power between sub-round operations. For example, FIG. 14 may be a power waveform graph according to the operations of the encryption device of FIG. 11. FIG. 14 shows an example of a power waveform graph when a real sub-round operation and virtual sub-round operations are performed at a ratio of 1:3. However, this is merely an example for convenience of explanation, and example embodiments are not limited thereto.

Referring to FIG. 14, power consumed among continuous virtual sub-round operations VR may be the same as power consumed when virtual sub-round operations VR are switched to real sub-round operations RR, for example, in a 50% probability. Accordingly, since it is not commonly inferred that the real sub-round operations RR are performed before and after a portion where power is consumed at most, the stability of the encryption operation may be improved.

Also, the virtual sub-round operations VR may be randomly selected, and thus, it may not be commonly inferred that a certain operation is performed before and after a portion where power waveforms are low. Also, as a ratio of the virtual sub-round operations VR is greater than a ratio of the real sub-round operations RR, the interference about locations of the real round operations may be effectively prevented.

Figure 15:
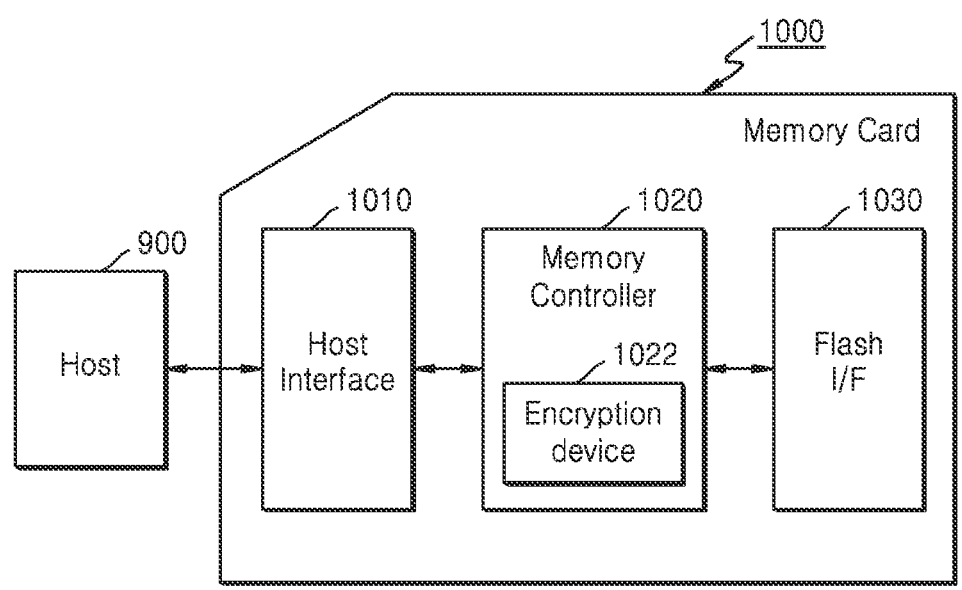
FIG. 15 is a block diagram of a memory card according to an example embodiment.

FIG. 15 is a block diagram of a memory card 1000 according to an example embodiment.

Referring to FIG. 15, the memory card 1000 may include a host interface 1010, a memory controller 1020, and a flash memory interface (Flash I/F) 1030. Also, the memory controller 1020 may further include an encryption device 1022 according to an example embodiment.

The host interface 1010 may perform interfacing with a host 900 based on a card protocol so as to exchange various types of data between the host 900 and the memory card 1000. The memory card 1000 may be applied to a Multimedia Card (MMC), a Security Digital (SD) card, a mini SD card, a Memory Stick, smartmedia, a TransFlash card, or the like. The memory controller 1020 may receive/transmit data from/to a flash memory (not illustrated) through the flash memory interface 1030. The flash memory may be a nonvolatile memory, for example, a NAND flash memory. The memory controller 1020 may control various operations of the flash memory through the flash memory interface 1030. The memory card 1000 includes the encryption device 1022 according to an example embodiment, and a real operation part is not specified despite a side channel attack on the memory card 1000. Accordingly, the stability of the memory card 1000 may be improved.

While the inventive concept has been particularly shown and described with reference to example embodiments thereof, it will be understood that various changes in form and details may be made therein without departing from the spirit and scope of the following claims.

What is claimed is:

1. A method of operating an encryption device, the method comprising:
    performing a plurality of virtual operations comprising an encryption operation using at least one of dummy data or a dummy encryption key;
    when a real operation request signal is received while a current virtual operation of the plurality of virtual operations is in progress, continuing to perform the current virtual operation;
    in response to an end of the current virtual operation, without stopping the encryption operation performing a real operation in which the encryption operation is performed, based on data to be encrypted and an encryption key associated with the data to be encrypted, that is requested by the real operation request signal,
    wherein the plurality of virtual operations are performed to mask the real operation.

2. The method of claim 1, further comprising receiving a delay number from outside of the encryption device,
    wherein
    in response to the end of the current virtual operation, continuing to perform the plurality of current virtual operations a number of times equal to the delay number before the real operation is performed.

3. The method of claim 2, wherein the delay number comprises a value received from a host outside the encryption device.

4. The method of claim 2, wherein the delay number comprises a random value received from a random value generator outside the encryption device.

5. The method of claim 1, wherein each of the plurality of virtual operations and the real operation comprises a plurality of round operations, and
    one round of the virtual operation and one round of the real operation each comprise a plurality of sub-round operations.

6. The method of claim 5, wherein the plurality of sub-round operations are classified into real sub-round operations and virtual sub-round operations, and
    the method further comprises forming a plurality of rounds, each comprising a real sub-round operation and a plurality of virtual sub-round operations of a first number.

7. The method of claim 6, wherein the encryption device further comprises a counter and a real sub-round operation register configured to store a random value, and
    the forming of the plurality of rounds comprises:
    initializing the counter and the random value and starting forming a first round;
    sequentially counting, by the counter, the plurality of sub-round operations and deriving a count value;
    performing the real sub-round operation when the count value is equal to the random value, and performing one virtual sub-round operation when the count value is different from the random value; and
    completing the first round when the count value is equal to a reference count value.

8. The method of claim 6, wherein the first number is a value obtained by 2$n$-1, where n is a positive integer.

9. The method of claim 6, wherein the virtual operation comprises the encryption operation based on the dummy data and the dummy encryption key, and
    wherein the encryption device comprises a plurality of virtual operation registers, each of which is configured to store the dummy data and the dummy encryption key on which the virtual sub-round operations are based.

10. The method of claim 9, further comprising:
    receiving a plurality of random bits;
    selecting one of the plurality of virtual operation registers, based on the plurality of random bits; and
    performing a sub-round operation based on the dummy data and the dummy encryption key stored in the one of the plurality of virtual operation registers.

11. A method of operating an encryption device for performing a virtual operation and a real operation, each of which comprises a plurality of round operations each comprising a plurality of sub-round operations classified into real sub-round operations and virtual sub-round operations, the method comprising:

initializing a count value and a random value regarding the plurality of sub-round operations and starting forming a round comprising the plurality of sub-round operations including one real sub-round operation of an encryption operation based on data to be encrypted and an encryption key associated with the data to be encrypted and a plurality of virtual sub-round operations of the encryption operation based on at least one of dummy data or a dummy encryption key;

deriving the count value by counting the plurality of sub-round operations;

without stopping the encryption operation performing the one real sub-round operation when the count value is equal to the random value, and one of the plurality of virtual sub-round operations when the count value is different from the random value; and when the count value is equal to a reference count value, completing the round, wherein the virtual operation is performed to mask the real operation.

12. The method of claim 11, wherein a sum of a first number of times that the one real sub-round operation is performed and a second number of times that the plurality of virtual sub-round operations are performed is equal to 2n, where n is a positive integer, and wherein the one real sub-round operation and the plurality of virtual sub-round operations are comprised in the round.

13. The method of claim 11, further comprising:

without stopping the encryption operation performing the virtual operation;

when a real operation request signal is received, determining whether the plurality of round operations comprised in the virtual operation, which is being performed, are completed; and in response to the plurality of round operations being completed, performing the real operation in response to the real operation request signal.

14. The method of claim 13, further comprising receiving a delay number from the outside of the encryption device, wherein the performing of the real operation comprises:

in response to the plurality of round operations being completed, without stopping the encryption operation performing the virtual operation a number of times equal to the delay number before the real operation is performed.

15. The method of claim 11, wherein the encryption device comprises a first virtual operation register and a second virtual operation register, each of which is configured to store the dummy data and the dummy encryption key on which the plurality of virtual sub-round operations are based, wherein the method further comprises:

selecting one of the first virtual operation register and the second virtual operation register based on a random bit; and performing a sub-round operation based on the dummy data and the dummy encryption key stored in the selected one of the first virtual operation register and the second virtual operation register.

16. The method of claim 15, wherein the random value comprises the random bit.

17. An encryption device for performing a virtual operation and a real operation, each comprising a plurality of round operations each comprising a plurality of sub-round operations classified into real sub-round operations of an encryption operation based on data to be encrypted and an encryption key corresponding to the data to be encrypted and virtual sub-round operations of the encryption operation based on at least one of dummy data or a dummy encryption key, the encryption device comprising:

a first virtual operation register configured to store first dummy data and a first dummy encryption key on which the virtual sub-round operations are based;

a second virtual operation register configured to store second dummy data and a second dummy encryption key on which the virtual sub-round operations are based; and a first multiplexer configured to receive a first output from the first virtual operation register and a second output from the second virtual operation register, without stopping the encryption operation select one of the first output or the second output based on a random bit, and output the one of the first output or the second output that is selected, wherein the virtual operation is performed to mask the real operation.

18. The encryption device of claim 17, further comprising:

a real operation register configured to store real data and a real encryption key on which the real sub-round operations are based; and a second multiplexer configured to receive a third output from the real operation register and a fourth output from the first multiplexer, without stopping the encryption operation select one of the third output or the fourth output in response to a real sub-round operation performance signal, and output the one of the third output or the fourth output that is selected.

19. The encryption device of claim 17, further comprising:

a data function module configured to perform the encryption operation based on the virtual operation and the real operation; and an encryption/decryption controller configured to receive a delay number from the outside of the encryption device, and when the data function module receives a real operation performance request while the virtual operation is being performed, without stopping the encryption operation control the data function module to perform the virtual operation a number of times equal to the delay number.

20. The encryption device of claim 17, wherein each of the plurality of round operations comprises one real sub-round operation and a plurality of virtual sub-round operations.

* * * * *